(12) United States Patent
Inagaki et al.

(10) Patent No.: US 12,178,259 B2
(45) Date of Patent: Dec. 31, 2024

(54) TEMPERATURE CONTROLLED AEROSOL SUPPLY DEVICE (71) Applicant: Japan Tobacco Inc., Tokyo (JP)

(72) Inventors: Michihiro Inagaki, Tokyo (JP); Yuki Abe, Tokyo (JP); Miki Wakamatsu, Tokyo (JP); Tatsuya Suganuma, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 529 days.

(21) Appl. No.: 17/495,538

(22) Filed: Oct. 6, 2021

(65) Prior Publication Data

US 2022/0022551 A1    Jan. 27, 2022

Related U.S. Application Data

(63) Continuation of application No. PCT/JP2020/014315, filed on Mar. 27, 2020.

(30) Foreign Application Priority Data

Apr. 9, 2019  (JP) .................................. 2019-074361

(51) Int. Cl.
*A24F 40/57* (2020.01)
*A24F 40/10* (2020.01)
(Continued)

(52) U.S. Cl.
CPC .............. *A24F 40/57* (2020.01); *A24F 40/10* (2020.01); *A24F 40/46* (2020.01); *A24F 40/48* (2020.01); *A24F 40/51* (2020.01); *B05B 17/0676* (2013.01)

(58) Field of Classification Search
CPC .......... A24F 40/57; A24F 40/10; A24F 40/46; A24F 40/48; A24F 40/51; B05B 17/0676
See application file for complete search history.

(56) References Cited

U.S. PATENT DOCUMENTS 3,885,902 A    5/1975  Fujieda et al.
7,516,714 B2 *  4/2009  Yamagata ................. B05B 5/00
                                                118/301
(Continued)

FOREIGN PATENT DOCUMENTS

EP    1 452 239 A1    9/2004
EP       3871530 A1 *  9/2021 ............... A24D 1/20
(Continued)

OTHER PUBLICATIONS

Translated "The Second Office Action" for CN 202080027640, dated Jun. 10, 2023, (Year: 2023).*

(Continued)

*Primary Examiner* — Michael H. Wilson
*Assistant Examiner* — Ardith Elyse Hertzog
(74) *Attorney, Agent, or Firm* — Birch, Stewart, Kolasch & Birch, LLP (57) ABSTRACT

An aerosol supply device includes: an accommodating part (cartridge) configured to accommodate a liquid; an atomization unit having a storing part to store the liquid, the atomization unit being configured to generate an aerosol by atomizing the liquid; and a temperature control part configured to control the temperature of the liquid at a given location between the accommodating part (cartridge) and the storing part.

12 Claims, 5 Drawing Sheets

(51) Int. Cl.
*A24F 40/46* (2020.01)
*A24F 40/48* (2020.01)
*A24F 40/51* (2020.01)
*B05B 17/06* (2006.01)

(56) References Cited

U.S. PATENT DOCUMENTS

| | | | |
|---|---|---|---|
| 11,063,452 B2* | 7/2021 | He | H02J 7/0045 |
| 2019/0230982 A1* | 8/2019 | Inagaki | A24B 15/32 |
| 2020/0329774 A1* | 10/2020 | Campitelli | A24F 40/42 |
| 2021/0022391 A1* | 1/2021 | Minami | B05B 17/06 |
| 2021/0022406 A1* | 1/2021 | Minami | A24F 40/57 |
| 2021/0030069 A1* | 2/2021 | Minami | B05B 17/0607 |
| 2021/0076734 A1* | 3/2021 | Minami | A24F 40/50 |

FOREIGN PATENT DOCUMENTS

| | | | | |
|---|---|---|---|---|
| JP | 4-236962 A | 8/1992 | | |
| JP | 5-22057 U | 3/1993 | | |
| JP | 2009-652 A | 1/2009 | | |
| JP | 2011-89684 A | 5/2011 | | |
| JP | 2012-24646 A | 2/2012 | | |
| JP | 2015-16407 A | 1/2015 | | |
| KR | 10-2007-0012985 A | 1/2007 | | |
| WO | WO-2017167521 A1 * | 10/2017 | | A24B 15/167 |
| WO | WO-2019198688 A1 * | 10/2019 | | A24F 40/05 |
| WO | WO-2020084773 A1 * | 4/2020 | | A24D 1/20 |

OTHER PUBLICATIONS

Google Machine Translation of JPH0522057U, 2023 (Year: 2023).*
International Search Report for PCT/JP2020/014315 mailed on Jun. 16, 2020.
Partial Supplementary European Search Report for European Application No. 20787488.4, dated Nov. 18, 2022.

* cited by examiner

TEMPERATURE CONTROLLED AEROSOL SUPPLY DEVICE

CROSS REFERENCE TO RELATED APPLICATIONS

This application is a Continuation of PCT International Application No. PCT/JP2020/014315, filed on Mar. 27, 2020, which claims priority under 35 U.S.C. 119(a) to Patent Application No. 2019-074361, filed in Japan on Apr. 9, 2019, all of which are hereby expressly incorporated by reference into the present application.

TECHNICAL FIELD

The present invention relates to an aerosol supply device configured to supply an aerosol of an atomized liquid.

BACKGROUND ART

Aerosol supply devices such as flavor inhalers capable of delivering flavor without combustion of a flavor source such as tobacco are now in widespread use.

Other known examples of aerosol supply devices include inhalers capable of atomizing a liquid by using ultrasonic waves for supply to the user.

PTL 1 discloses an aerosol supply device (referred to as "liquid atomizing apparatus" in PTL 1) configured to generate an aerosol by use of a surface acoustic wave (also referred to as SAW).

More specifically, the aerosol supply device described in PTL 1 atomizes a liquid supplied from each liquid feeder via a supply port, by using a surface acoustic wave generated by a piezoelectric substrate and comb-shaped electrodes formed on the piezoelectric substrate.

CITATION LIST

Patent Literature

PTL 1: Japanese Patent Application Publication No. 2012-024646

SUMMARY OF INVENTION

Technical Problem

With regard to atomization of a liquid, the viscosity/surface tension of a liquid varies with the temperature of the liquid, which leads to fluctuations in the rate of atomization. More specifically, changes in the viscosity/surface tension of a liquid cause changes in the degree of waviness of the liquid surface and the manner in which the liquid particles separate. For this reason, the rate of atomization may fluctuate even for the same electric power supplied to the comb-shaped electrodes and for the same surface acoustic wave energy propagated to the liquid. In other words, for the same electric power supplied to the comb-shaped electrodes, the rate at which a liquid is atomized decreases with increasing viscosity of the liquid or with decreasing surface tension of the liquid.

In this regard, the aerosol supply device described in PTL 1 includes no temperature control mechanism. This makes the aerosol supply device susceptible to the influence of ambient temperature, which may result in decreased rate of atomization.

Further, if a liquid freezes under low outside air temperature conditions, this may, in some cases, make it impossible to generate an aerosol due to the inability to supply the liquid onto the piezoelectric substrate.

The present invention has been made in view of the above-mentioned problems. Accordingly, it is an object of the present invention to provide an aerosol supply device capable of stabilizing the rate of liquid atomization to allow for stable aerosol supply.

Solution to Problem

An aerosol supply device according to the present invention includes: an accommodating part configured to accommodate a liquid; an atomization unit having a storing part to store the liquid supplied from the accommodating part, the atomization unit being configured to generate an aerosol by atomizing the liquid stored in the storing part; and a temperature control part configured to control a temperature of the liquid at a given location between the accommodating part and the storing part.

Advantageous Effects of Invention

The aerosol supply device according to the present invention allows for stable supply of a liquid to the atomization unit to provide stable supply of an aerosol to the outside of the aerosol supply device.

BRIEF DESCRIPTION OF DRAWINGS

FIG. 1 schematically illustrates the configuration of an aerosol supply device according to the embodiment presented herein.

FIG. 2 schematically illustrates a liquid being atomized and discharged to the outside of the aerosol supply device.

FIG. 3 is a plan view of an atomization unit.

FIG. 4 schematically illustrates an aerosol supply device including a Peltier element and a temperature sensor, in accordance with a first modification.

FIG. 5 schematically illustrates a housing with a urethane foam attached thereto, and an external-heat conduction part, in accordance with a second modification.

DESCRIPTION OF EMBODIMENTS

Embodiments of the present invention are described below with reference to the drawings. The following description of the embodiments is illustrative only for purposes of better understanding the present invention, and not to be taken as limiting the present invention. It is to be readily appreciated, therefore, that the shapes, arrangements, materials, or other details of components or parts described below may be changed or modified without departing from the scope of the present invention, and that all such equivalents fall within the scope of the present invention.

Throughout the drawings, like components are designated by like reference signs, and overlapping descriptions are omitted as appropriate.

<Overview>

An overview of an aerosol supply device 1 according to the embodiment is first described below with reference to FIGS. 1 and 2. FIG. 1 schematically illustrates the configuration of the aerosol supply device 1 according to the embodiment. FIG. 2 schematically illustrates a liquid 10 being atomized and discharged to the outside of the aerosol supply device 1. Although gaskets or other packing materials are provided between various components of the aerosol supply device 1 from the viewpoint of ensuring hermetic sealing, some of such packing materials are not depicted in FIG. 2 or other figures to facilitate understanding of the present invention.

The aerosol supply device 1 according to the embodiment includes an accommodating part (a cartridge (4)), an atomization unit 5, and a temperature control part (a piezoelectric substrate 5a, an electrode 5c, and an element-heat conduction part 40). The accommodating part is configured to accommodate the liquid 10. The atomization unit 5 has a storing part 5b to store the liquid 10 supplied from the accommodating part (cartridge 4). The atomization unit 5 generates an aerosol 11 by atomizing the liquid 10 stored in the storing part 5b. The temperature control part controls the temperature of the liquid 10 at a given location between the accommodating part (cartridge 4) and the storing part 5b.

In particular, disposing the temperature control part in the form of a heat conduction part, a heat source, or a cooling part directly at "a given location between the accommodating part and the storing part 5b" is preferred because this allows the temperature of the liquid 10 to be efficiently controlled through supply or absorption of heat.

According to the above-mentioned configuration, by controlling the temperature of the liquid 10 as the liquid 10 travels from the accommodating part to the storing part 5b, the rate of atomization of the liquid 10 can be stabilized irrespective of outside air temperature, which allows for stable supply of the aerosol 11 to the outside of the aerosol supply device 1.

First Embodiment

<Configuration of Various Parts>

The configuration of various parts of the aerosol supply device 1 is now described below with reference to FIG. 3 in addition to FIGS. 1 and 2. FIG. 3 is a plan view of the atomization unit 5.

The aerosol supply device 1 according to a first embodiment supplies the aerosol 11 by atomizing the liquid 10 by vibration (surface acoustic wave). As for the "vibration" mentioned above, using a surface acoustic wave is preferred from the viewpoint of atomization because of the ability to propagate vibration at a high frequency. However, this is not meant to be limiting. Alternatively, the vibration used may be such that the entire object to be vibrated (vibrating element) vibrates.

(Atomization Unit)

As illustrated in FIGS. 2 and 3, the atomization unit 5 includes a vibrating element (piezoelectric substrate 5*a*) configured to vibrate the liquid 10 to create the aerosol 11, and a vibration source (electrode 5*c*) configured to, in response to receiving supply of electric power, vibrate the vibrating element.

In particular, according to this embodiment, the "vibrating element" is the piezoelectric substrate 5*a* having a piezoelectric element, and the "vibration source" is the electrode 5*c* having a comb shape. The electrode 5*c* generates a surface acoustic wave on the piezoelectric substrate 5*a*.

The above-mentioned configuration allows for efficient utilization of the energy required for atomization based on the surface acoustic wave.

(Piezoelectric Substrate)

The piezoelectric substrate 5*a* according to this embodiment is made of lithium niobate including a piezoelectric element. The piezoelectric substrate 5*a* has the storing part 5*b* to store the liquid 10.

As illustrated in FIG. 3, the storing part 5*b* provided to the piezoelectric substrate 5*a* according to this embodiment is a closed-end groove having an elliptical shape in plan view that is formed on the top surface of the piezoelectric substrate 5*a*. The storing part 5*b* is disposed in at least two places, with the electrode 5*c* being disposed between the two places. The storing part 5*b* has a through-hole 5*d* provided in the central portion such that the through-hole 5*d* extends through the thickness of the piezoelectric substrate 5*a*. The storing part 5*b* receives the liquid 10 that is supplied from the cartridge 4 via a first passage 6 (tube 6*a*) and the through-hole 5*d* by means of a pump 9 described later.

(Electrode)

The electrode 5*c* is disposed in contact with the piezoelectric substrate 5*a* to supply a surface acoustic wave to the liquid 10 stored in the storing part 5*b* disposed on the piezoelectric substrate 5*a*.

The electrode 5*c* is a comb-shaped electrode (also referred to as interdigital transducer (IDT)). High-frequency electric power input from a power board 13 to the electrode 5*c* via a control board 12 is converted into a surface acoustic wave (also referred to as SAW) due to the piezoelectricity of the piezoelectric substrate 5*a*, and propagates along the surface of the piezoelectric substrate 5*a* on both sides in the direction of arrangement of the comb teeth.

The number of comb teeth of the electrode 5*c* is not limited to the number depicted but is determined based on the efficiency of atomization by which the aerosol 11 is produced by using a surface acoustic wave. The width and spacing of the comb teeth are determined based on a frequency based on the particle size of the aerosol 11 to be produced by atomization.

An important consideration with regard to a surface acoustic wave is the control of the frequency of electric power. Accordingly, sensors such as a resonant-frequency monitoring sensor for monitoring resonant frequency, or a temperature sensor (not illustrated) capable of detecting the temperature of the liquid 10 immediately before atomization may be provided.

The exterior construction of the aerosol supply device 1 according to this embodiment mainly includes a device body 2, and a mouthpiece 3 attached to an upper portion of the device body 2 and through which the aerosol 11 is to be discharged.

(Element-Heat Conduction Part)

The aerosol supply device 1 further includes the element-heat conduction part 40. The element-heat conduction part 40 has thermal conductivity, and is connected to the vibrating element (piezoelectric substrate 5*a*) and to the accommodating part (cartridge 4). As used herein, the expression "having thermal conductivity" means being highly thermally conductive. Accordingly, the element-heat conduction part 40 is made of a material such as copper, aluminum, or carbon. More specifically, the element-heat conduction part 40 has a higher thermal conductivity than another component (which is, for example, the tube 6*a* in this embodiment) that is in contact with the liquid 10 between the piezoelectric substrate 5*a* and the cartridge 4.

The "temperature control part" according to the present invention includes the vibrating element (piezoelectric substrate 5*a*), the vibration source (electrode 5*c*), and the element-heat conduction part 40.

The above-mentioned configuration makes it possible to dissipate, by means of the element-heat conduction part 40, the heat of the piezoelectric substrate 5*a* that is generated in association with the vibration generated from the electrode 5*c* and propagated to the vibrating element (piezoelectric substrate 5*a*) to atomize the liquid 10. This helps to reduce breakage of the vibrating element (piezoelectric substrate 5*a*) caused by application of heat. Further, the accommodating part (cartridge 4) can be heated. This helps to ensure that even under low temperature environment, the liquid 10 does not freeze within the cartridge 4, which allows for stable aerosol supply by the aerosol supply device 1.

(Thermostat)

The aerosol supply device 1 according to this embodiment includes a thermostat 41. The thermostat 41 is capable of physically connecting and disconnecting the piezoelectric substrate 5*a* and the element-heat conduction part 40 in accordance with the internal temperature of the aerosol supply device 1.

The thermostat 41 has the function of, when a temperature greater than or equal to a predetermined temperature is reached, delivering heat generated in the piezoelectric substrate 5*a* to the cartridge 4. For example, the thermostat 41 used is one that utilizes changes in the shape of a bimetal element or changes in the volume of a wax. Under normal usage condition such as at the beginning of its use, the thermostat 41 physically disconnects the piezoelectric substrate 5*a* and the element-heat conduction part 40.

To atomize the liquid 10, an alternating-current voltage is applied from the electrode 5*c* to the piezoelectric substrate 5*a*. This results in a SAW being generated on the piezoelectric substrate 5*a*, which causes the temperature of the piezoelectric substrate 5*a* to rise. Once a temperature greater than or equal to a predetermined temperature is reached, the thermostat 41 automatically operates to physically connect the piezoelectric substrate 5*a* and the element-heat conduction part 40.

The above-mentioned configuration is preferred because this allows the temperature of the piezoelectric substrate 5*a* to be easily maintained within a predetermined temperature range by means of the thermostat 41. This facilitates stabilization of atomization rate.

In an alternative configuration, the thermostat 41 may not be used. Instead, a controller 12*a* described later may be configured to, in response to a signal associated with a temperature detected by a temperature sensor 49 described later with reference to FIG. 4, drive an actuator (not illustrated) to bring the element-heat conduction part 40 into contact with the piezoelectric substrate 5*a*.

In one example, the controller 12*a* may be configured to, in response to the temperature sensor 49 detecting a temperature determined to be the temperature at which the liquid 10 within the cartridge 4 freezes, control the element-heat conduction part 40 into contact with the piezoelectric substrate 5*a*.

The above-mentioned configuration is not meant to be limiting. In a still another example, the piezoelectric substrate 5*a* and the element-heat conduction part 40 may be configured to be connected at all times.

The thermostat 41 may not necessarily be designed to dissipate heat from the piezoelectric substrate 5*a* through the above-mentioned mechanical action. In one alternative example, the controller 12*a* may utilize the on/off state of an electrical signal provided from the thermostat 41 to switch the directions of current through a Peltier element 48 described later with reference to FIG. 4, to thereby make the Peltier element 48 function as a cooler or function as a heater.

(Mouthpiece)

The mouthpiece 3 according to this embodiment is formed such that, in front view, the mouthpiece 3 extends to be wider in an end portion near the bottom, and has a tapered part with a width that decreases toward a discharge port 3*a* located at the top end of the mouthpiece 3 and through which the aerosol 11 is to be discharged externally.

Figure 2:
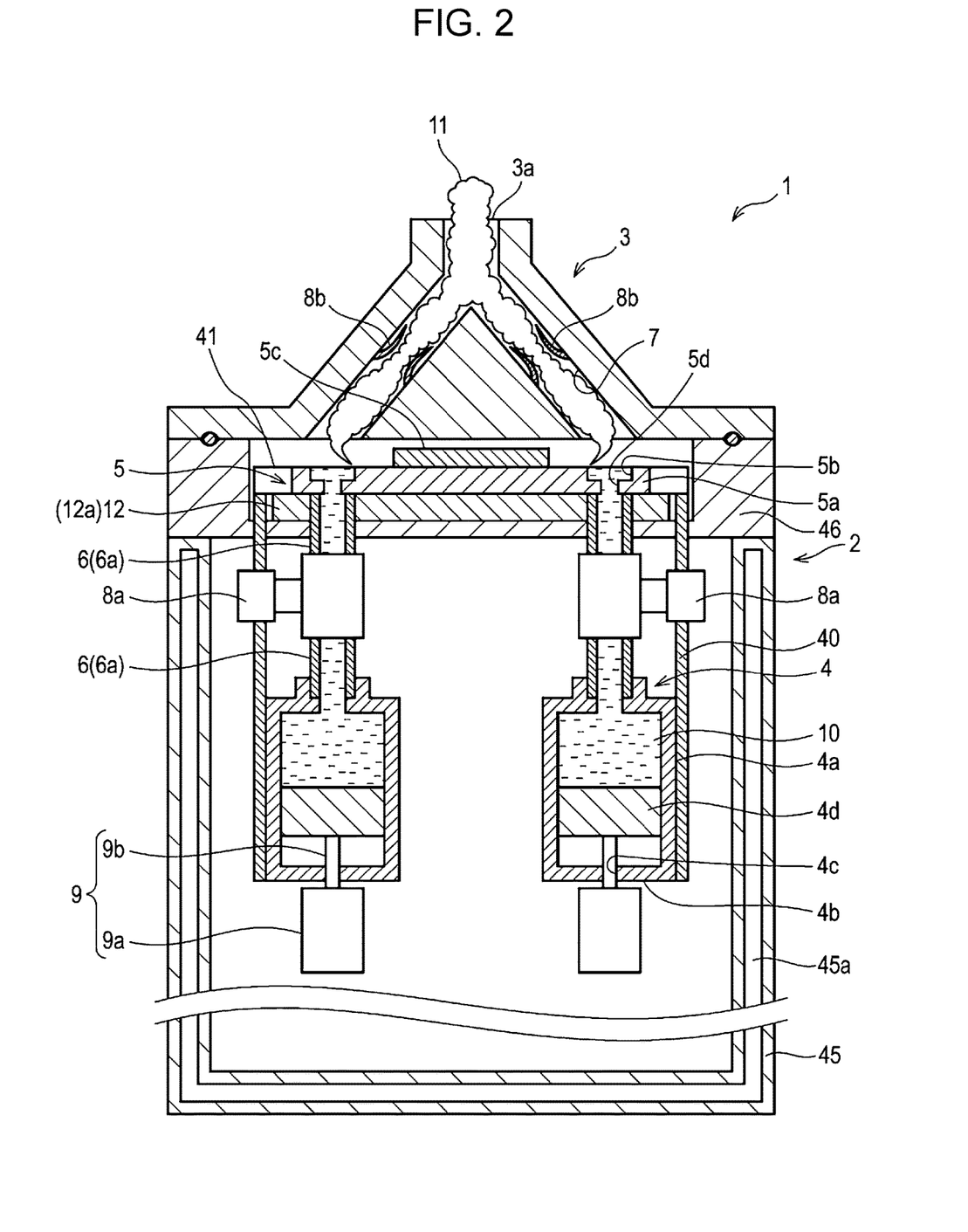
Figure 3:
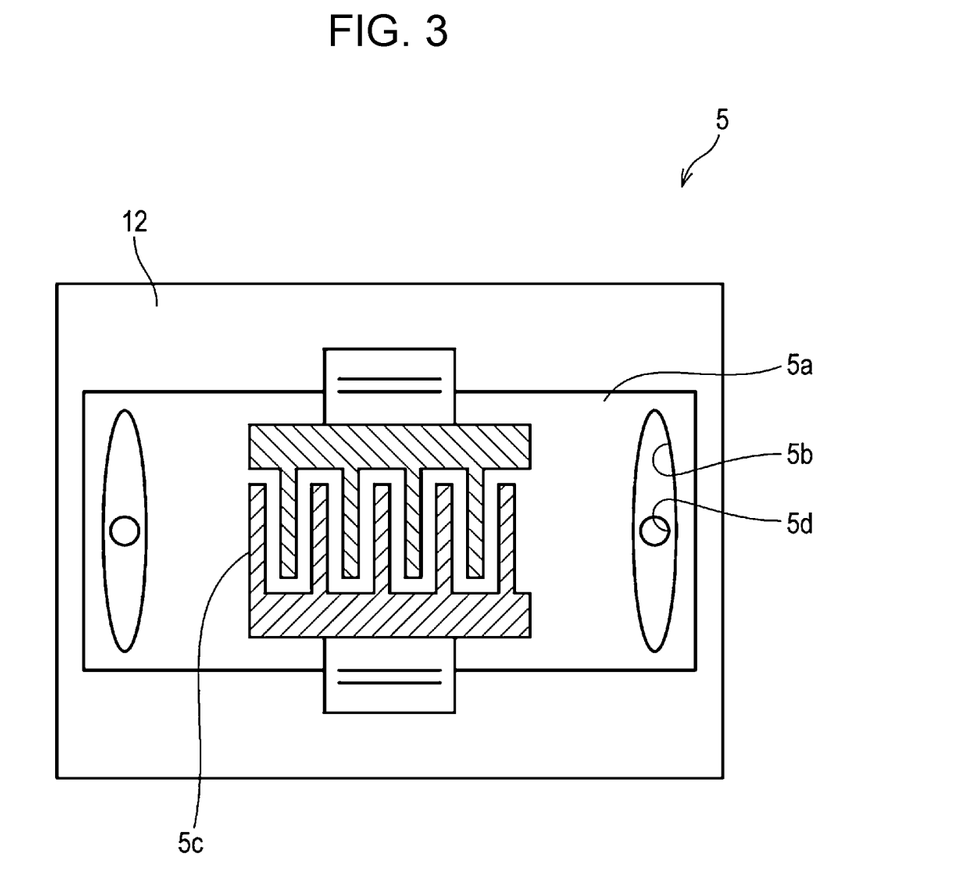

As illustrated in FIG. 2, the mouthpiece 3 has a passage (second passage 7) through which to pass the aerosol 11 generated from the atomization unit 5. The passage (second passage 7) includes two separate passages each disposed to allow passage of the aerosol 11 generated from the liquid 10 stored in the storing part 5*b* disposed in the at least two places. The two second passages 7 are formed symmetrically with respect to an imaginary plane passing through the discharge port 3*a*. The two second passages 7 join into a single passage immediately before reaching the discharge port 3*a* located at the top end of the mouthpiece 3.

The separate passages (second passages 7) may be formed to have different lengths. In other words, the two second passages 7 may not necessarily be formed symmetrically with respect to the imaginary plane passing through the discharge port 3*a* but may be formed asymmetrically. For example, if the two second passages 7 allow passage of aerosols 11 containing different components, each passage may be formed with a length or shape appropriate to the corresponding aerosol 11.

In a particularly preferred example for such separate second passages 7, the second passages 7 include an asymmetric portion. The asymmetric portion is formed, for example, by a curvature of one of the two second passages 7 that is different from that of the other one of the two second passages 7.

According to the above-mentioned configuration, by bringing the aerosol 11 into contact with a wall surface defining the asymmetric portion of the two second passages 7 with different curvatures, particles contained in the aerosol can be deposited/reduced, and their particle size can be adjusted. This allows the user to smoothly inhale the aerosol 11 without experiencing discomfort in the throat caused by components contained in the aerosol 11.

The term "curvature" as used herein is meant to conceptually include not only sharp bends but also gentle bends. Examples of two second passages 7 with different curvatures include not only two passages that are both bent but also two passages including one straight passage.

The mouthpiece 3 according to this embodiment includes a duckbill valve 8*b*, and the second passage 7 that splits into two passages. However, the mouthpiece 3 may not necessarily be configured as described above.

In one alternative example, the mouthpiece 3 may not include the duckbill valve 8*b*, and may be configured such that a single second passage 7 is disposed in contiguity with a single passage (first passage 6) through which the liquid 10 is supplied from the cartridge 4.

The above-mentioned configuration makes it possible to shorten the second passage 7 through which the aerosol 11 generated from the atomization unit 5 travels before reaching the discharge port 3*a*. Shortening the second passage 7 in this way helps to reduce condensation of the aerosol 11.

(Device Body)

Figure 1:
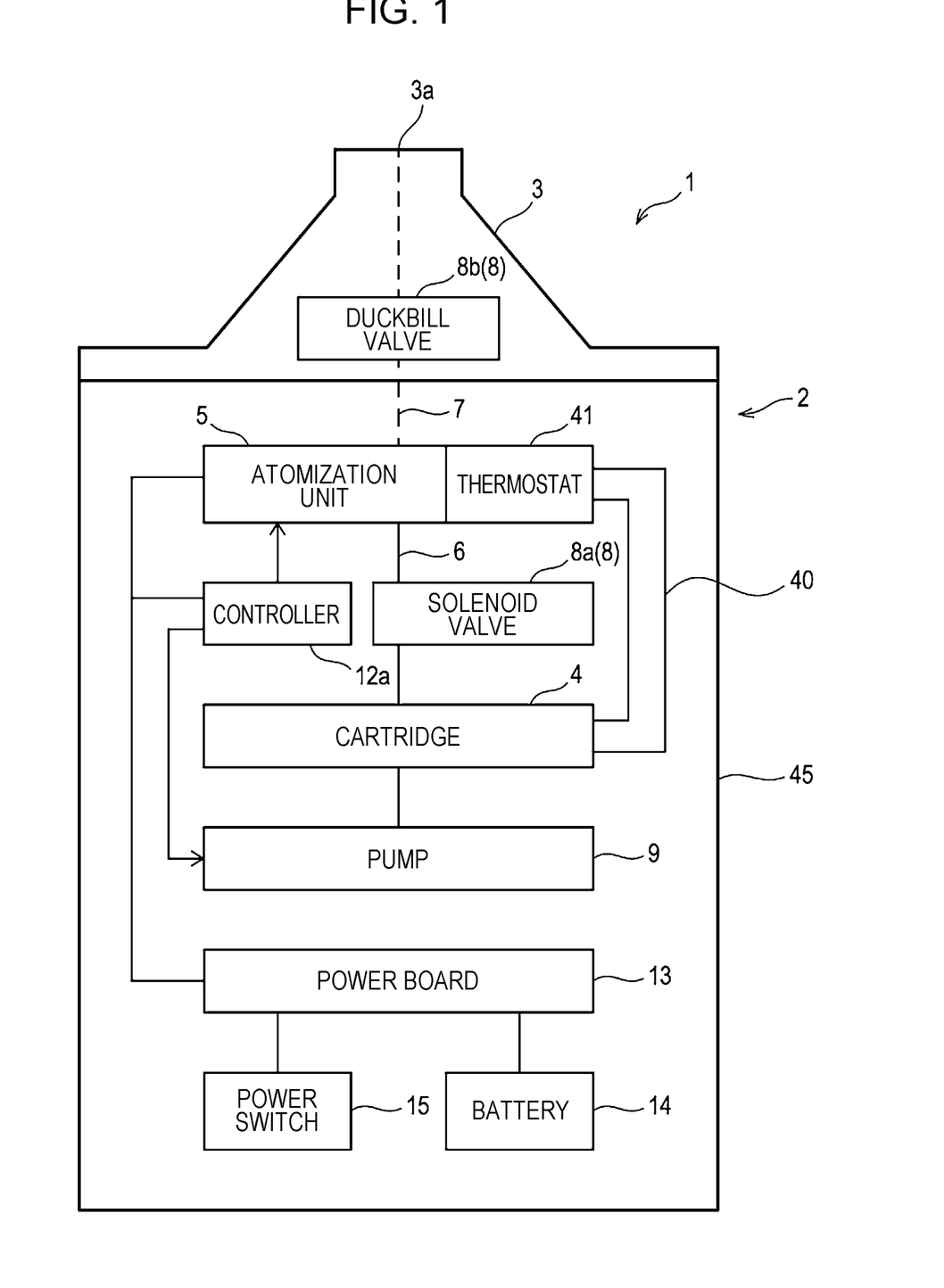

As illustrated in FIGS. 1 and 2, the device body 2 includes a housing 45, and a lid 46. The housing 45 accommodates components including: the cartridge 4; a solenoid valve 8*a*; the pump 9; the control board 12 including the controller 12*a*; the power board 13; and a battery 14. The lid 46 is attached to the top open end portion of the housing 45, and has a recess in its upper end portion to accommodate the atomization unit 5. The device body 2 is provided with a power switch 15 exposed to the outside of the device body 2.

The device body 2 has a passage (first passage 6) for the liquid 10 that is defined between the cartridge 4, which will be described later, and the atomization unit 5. Further, the passage (second passage 7) for the aerosol 11 is defined between the atomization unit 5 and the outside of the device body 2 so as to extend from the device body 2 to the mouthpiece 3.

(Housing)

The housing 45 according to this embodiment includes a heat insulation structure (vacuum area 45a), which is provided between the accommodating part (cartridge 4) and the outside of the aerosol supply device 1 and has a lower thermal conductivity than the cartridge 4. More specifically, the heat insulation structure includes the vacuum area 45a, which is a vacuumed space defined between the inner and outer layers of the housing 45.

The term "vacuum" as used herein refers to "the state of a space filled with gas with a pressure lower than atmospheric pressure", and is meant to permit the presence of trace amounts of molecules. The presence of the vacuum area 45a results in extremely low thermal conductivity, which contributes to heat insulation. This helps to reduce the influence of outside air temperature on the liquid 10 within the cartridge 4.

(Cartridge)

The cartridge 4 according to this embodiment includes a body part 4a, a base plate 4b, and a sliding block 4d. The base plate 4b is integrated with the bottom portion of the body part 4a. The sliding block 4d is disposed inside the cartridge 4, and arranged in a watertight manner on the inner wall surface of the body part 4a. The sliding block 4d is capable of sliding within the body part 4a.

The base plate 4b has a through-hole 4c extending through the thickness of the base plate 4b. A push rod 9b of the pump 9, which will be described later, can be inserted into the through-hole 4c.

According to the this embodiment, the liquid 10 can be supplied separately from each of two cartridges 4 to the corresponding one of two storing parts 5b provided to the piezoelectric substrate 5a of the atomization unit 5.

However, the present invention is not limited to this configuration. Alternatively, the liquid 10 may be supplied from a single cartridge 4 to two storing parts 5b. This configuration makes it possible to reduce the number of solenoid valves 8a, which will be described later. That is, the solenoid valve 8a may be simply provided to a portion of the tube 6a near the cartridge 4, at a position before where the tube 6a splits in two toward the two storing parts 5b.

The above-mentioned configuration makes it possible to, by means of a single solenoid valve 8a, control whether to supply the liquid 10 to two storing parts 5b or stop the supply of the liquid 10.

The aerosol supply device 1 may further include a plurality of cartridges 4. If two or more cartridges 4 are to be used, individual cartridges 4 may accommodate liquids 10 with different components such as taste or fragrance.

The accommodating part according to the present invention may not necessarily be the cartridge 4 that is removable, but may be a container pre-installed on the device body 2 (i.e., a refillable container). If such a pre-installed container is to be used, the container may be filled with the liquid 10 in a similar manner. That is, another passage communicating with the container and the outside may be formed in advance, and the liquid 10 may be charged into the container through the other passage to fill the container with the liquid 10.

The above-mentioned configuration eliminates the need for the user to, when refilling the container with the liquid 10, remove pre-installed components including the solenoid valve 8a, the cartridge 4, and the tube 6a connecting the solenoid valve 8a and the cartridge 4, and attach these components again.

(Liquid)

The liquid 10 may include a solvent such as water, glycerol, propylene glycol, or ethanol. Further, the liquid 10 may include a solute containing a component such as taste or fragrance. Exemplary solvents include volatile components such as tobacco extracts, menthol, linalool, limonene, or vanillin, or non-volatile components, for example, sugars such as fructose, glucose, sucrose, or lactose, acids such as malic acids or citric acids, or salts.

The liquid 10 may be emulsified by an emulsifier, or may be suspended by a dispersant. An antifreeze component such as the glycerol, propylene glycol, or ethanol mentioned above may be added to the liquid 10 to produce an antifreeze solution with a melting point of less than or equal to −20 degrees Celsius, more preferably less than or equal to −30 degrees Celsius. The presence of such an antifreeze component in the liquid 10 helps to prevent the liquid 10 within the atomization unit 5 from freezing even when the outside environment is at low temperature, such as in winter.

(Volatilization Preventing Part)

The solenoid valve 8a, which is disposed between the tubes 6a, is connected to the tubes 6a that connect the cartridge 4 and the atomization unit 5 within the device body 2.

The solenoid valve 8a includes an open/close part (not illustrated) capable of opening and closing the first passage 6 through which the liquid 10 flows.

According to the configuration mentioned above, by the controller 12a operating the open/close part of the solenoid valve 8a to close the first passage 6, volatilization of the liquid 10 from the accommodating part (cartridge 4) can be prevented. Further, by the controller 12a operating the open/close part of the solenoid valve 8a to open the first passage 6, the liquid 10 can be supplied to the atomization unit 5, and consequently the aerosol 11 can be supplied to the user.

In the following description of this embodiment, the duckbill valve 8b constituting a check valve is described as an example of a volatilization preventing part 8 configured to open and close the passage for the aerosol 11. The duckbill valve 8b according to this embodiment is a valve including opposed flat plates made of a soft resin material, with the spacing between the flat plates decreasing progressively toward the downstream (suction) side. The duckbill valve 8b is configured such that in normal condition, the flat plates contact each other to close the passage, and when a suction pressure is applied from the downstream side, the flat plates move away from each other to open the passage.

The duckbill valve 8b acts as a small check valve to allow the passage for the aerosol 11 to narrow. This makes it possible to reduce the size of the mouthpiece 3 and therefore the size of the aerosol supply device 1. The duckbill valve 8b is preferred for its ability to open by a small suction force without being affected by the direction of gravity, and for its ability to naturally close the open/close part due to the elastic restoring force once the suction stops.

The two second passages 7 of the mouthpiece 3 are each provided with the volatilization preventing part 8 (duckbill valve 8b).

The volatilization preventing part (duckbill valve 8b) is disposed in each of the two passages at an equal distance from the discharge port 3a.

According to the above-mentioned configuration, the aerosol 11 generated from the storing part 5b disposed in two places can be discharged through the discharge port 3a at the same timing. This helps to reduce variations in the rate at which the aerosol 11 is discharged.

The volatilization preventing part 8 (duckbill valve 8b) is capable of transition between a state in which the volatilization preventing part 8 closes the passage (second passage 7) for the aerosol 11, and a state in which the volatilization preventing part 8 opens the passage (second passage 7) for the aerosol 11.

According to the above-mentioned configuration, closing the second passage 7 for the aerosol 11 by means of the duckbill valve 8b makes it possible to limit volatilization of the liquid 10 within a hermetically sealed space with the saturated vapor pressure of the liquid 10 as an upper limit to thereby inhibit precipitation of the solute on the atomization unit 5. This helps to reduce deterioration of atomization efficiency.

The volatilization preventing part 8 according to this embodiment is a valve element (duckbill valve 8b) configured to close the passage (second passage 7) for the aerosol 11 in a first state, and open the passage (second passage 7) for the aerosol 11 in a second state in which the pressure condition has changed due to suction applied by the user. The volatilization preventing part (duckbill valve 8b) is disposed between the storing part 5b and the discharge port 3a.

More specifically, the "first state" according to this embodiment refers to a state in which the air inside the aerosol supply device 1 is not being sucked by the user through the discharge port 3a. Conversely, the "second state" refers to a state in which the air inside the aerosol supply device 1 is being sucked by the user through the discharge port 3a.

According to the above-mentioned configuration, the open/close part is a valve element. Consequently, while suction is applied by the user, the aerosol 11 can be supplied to the user, and while suction is not applied by the user, the second passage 7 is closed to prevent volatilization of the liquid 10 to the external environment through the discharge port 3a.

Further, as described above, the aerosol supply device 1 that atomizes the liquid 10 by means of a surface acoustic wave includes the volatilization preventing part (duckbill valve 8b) disposed between the storing part 5b and the discharge port 3a. As a result, precipitation of the solute on the storing part 5b can be prevented. This helps to reduce variations in the concentration of the solute in the liquid 10, thus allowing stable taste or fragrance.

The "valve element" according to the present invention is not limited to the duckbill valve 8b. The valve element may be a solenoid valve similar to the solenoid valve 8a, an air-operated pinch valve with a tube closed by the pressure applied by supplied air, or an electrically driven valve. For example, if the electrically driven valve is to be used, a portion of the second passage 7 may be simply formed by a flexible tube to which the electrically driven valve can be connected.

By using an electrically driven valve instead of the duckbill valve 8b, the aerosol 11 can be discharged externally by the controller 12a controlling the opening action of the electrically driven valve, without the user having to suck on the discharge port 3a of the mouthpiece 3 and apply suction pressure. That is, an electrically driven valve is suited for use in diffusers that do not rely on the suction applied by the user to spray an aerosol. For example, the opening action of an electrically driven valve is controlled by the controller 12a in accordance with an operation performed on the power switch 15 as will be described later.

Although the duckbill valve 8b as a check valve has been described above as an exemplary "valve element", this is not meant to be limiting. The valve element may be any valve element capable of preventing volatilization due to its ability to close a passage in its normal state. For example, the valve element may be one capable of permitting backflow when positive pressure is being applied.

Likewise, the volatilization preventing part for opening and closing the first passage 6 is not limited to the solenoid valve 8a but may be an air-operated pinch valve with a tube closed by the pressure applied by supplied air, or an electrically driven valve.

In another example, the volatilization preventing part for opening and closing the first passage 6 or the second passage 7 may be one that is driven non-electrically. That is, the volatilization preventing part used may be one that causes the first passage 6 or the second passage 7 to be opened and closed by a physical drive action (movement of a barrier) (not illustrated) responsive to the user attaching the mouthpiece 3 to the device body 2 or pushing the mouthpiece 3 into the device body 2.

With no suction pressure applied, the duckbill valve 8b closes the second passage 7. This helps to prevent foreign matter from passing into the atomization unit 5 even if the foreign matter enters the aerosol supply device 1 through the discharge port 3a when the aerosol supply device 1 is not in use. Discharge of the aerosol 11 containing such foreign mater can be thus reduced, which proves advantageous also from the viewpoint of sanitation.

(Pump)

The aerosol supply device 1 further includes the pump 9 capable of supplying the liquid 10 to the atomization unit 5. The pump 9 according to this embodiment is a syringe pump capable of supplying the liquid 10 to the atomization unit 5 from the cartridge 4, and also pulling the liquid 10 back toward the accommodating part (cartridge 4) from the atomization unit 5.

Although described in more detail later, using a syringe pump as the pump 9 makes it possible to pull the liquid 10 back toward the accommodating part (cartridge 4) from the atomization unit 5.

By thus reducing the amount of the liquid 10 remaining on the atomization unit 5, precipitation of the solute on the atomization unit 5 can be reduced.

More specifically, the pump 9 includes a motor 9a, and the push rod 9b capable of advancing or retracting as the motor 9a rotates. As the pump 9 operates, the push rod 9b passes through the through-hole 4c and pushes in the sliding block 4d upward. At this time, the liquid 10 is pushed in by the sliding block 4d and supplied to the atomization unit 5.

If the pump 9 is a syringe pump as described above, by retracting the push rod 9b from the through-hole 4c of the cartridge 4, the liquid 10 can be pulled in the reverse direction. The liquid 10 can be thus pulled in to a position where the liquid 10 leaves the storing part 5b. This configuration is preferred for the ability to reduce precipitation of the solute on the storing part 5b.

For instance, there are cases where, if the liquid 10 contains citric acid mixed therein, the citric acid that has not turned into mist may precipitate out of the liquid 10 remaining in the storing part 5b and solidify. In this regard, by pulling the liquid 10 in the reverse direction from the storing part 5b by means of the pump 9 as described above, precipitation of citric acid on the storing part 5b is reduced to thereby reduce variations in the concentration of citric acid in the liquid 10. This allows stable taste or fragrance.

Further, the sliding block 4d that comes into contact with the liquid 10 is disposed in the cartridge 4. This means that the pump 9 (push rod 9b) does not directly contact the liquid 10. As a result, for instance, in changing different kinds of cartridges 4 to change the kind of the liquid 10 having taste or fragrance, even if the pump 9 is not replaced, mixing of components such as taste or fragrance do not occur before and after the changing of the cartridges 4.

However, the pump according to the present invention may not necessarily be configured as described above but may be, for example, a piezoelectric pump (not illustrated). Using a piezoelectric pump makes it possible to provide a product with low electric power consumption. In another example, the liquid 10 may be supplied by capillary action.

(Control Board)

The aerosol supply device 1 further includes the control board 12 having the controller 12a configured to control the electric power to be supplied to the vibration source (electrode 5c).

The controller 12a controls various electronics. In particular, the controller 12a controls the atomization unit 5 such that electric power is supplied to the electrode 5c to generate a surface acoustic wave on the surface of the piezoelectric substrate 5a.

The controller 12a also controls operations of components such as the pump 9 and the solenoid valve 8a. The controller 12a according to this embodiment changes the solenoid valve 8a from a closed state, which is a normal state, to an open state in response to receiving a signal transmitted from the power board 13 and indicating that the aerosol supply device 1 has been activated by the user operating the power switch 15.

Further, the controller 12a activates the motor 9a of the pump 9 to cause the push rod 9b to push in the sliding block 4d in a direction (upward) that diminishes the volume of the cartridge 4. Consequently, the liquid 10 is supplied to the storing part 5b through the first passage 6. The liquid 10 is thus resonated and atomized by a surface acoustic wave on the surface of the piezoelectric substrate 5a.

In this state, as the user sucks in the air inside the aerosol supply device 1 through the discharge port 3a, the pressure in a portion of the duckbill valve 8b near the discharge port 3a becomes negative. This causes the duckbill valve 8b to open, which allows the user to suck in the aerosol 11 passing through the duckbill valve 8b.

The controller 12a is configured to, when the aerosol supply device 1 becomes no longer used, for example, when the power switch 15 is switched off, operate the solenoid valve 8a (open/close part) to close the passage for the liquid 10.

In a particularly preferred example, the controller 12a is configured to, in closing the passage for the liquid 10 as described above, control the pump 9 such that the liquid 10 is supplied to the atomization unit 5 before the liquid 10 is pulled back toward the accommodating part (cartridge 4) from the atomization unit 5, and cause the open/close part (solenoid valve 8a) to close the passage for the liquid 10 supplied to the atomization unit 5.

According to the above-mentioned configuration, if the solute precipitates out on the atomization unit 5, the liquid 10 is supplied to the cartridge 4 to dissolve the solute again. Then, the liquid is pulled back toward the cartridge 4 from the atomization unit 5. This allows the amount of solute remaining on the atomization unit 5 to be reduced in comparison to a case where the liquid 10 is pulled back toward the cartridge 4 without being first supplied to the atomization unit 5. This helps to further reduce precipitation of the solute on the atomization unit 5 (piezoelectric substrate 5a).

In another alternative example, the controller 12a may be configured to, based on the amount of consumption of the liquid 10 per unit time as detected by a sensor (not illustrated), control the output of the pump 9 to change the speed at which to feed the push rod 9b, or control SAW output to stabilize the rate of atomization.

[First Modification]

Figure 4:
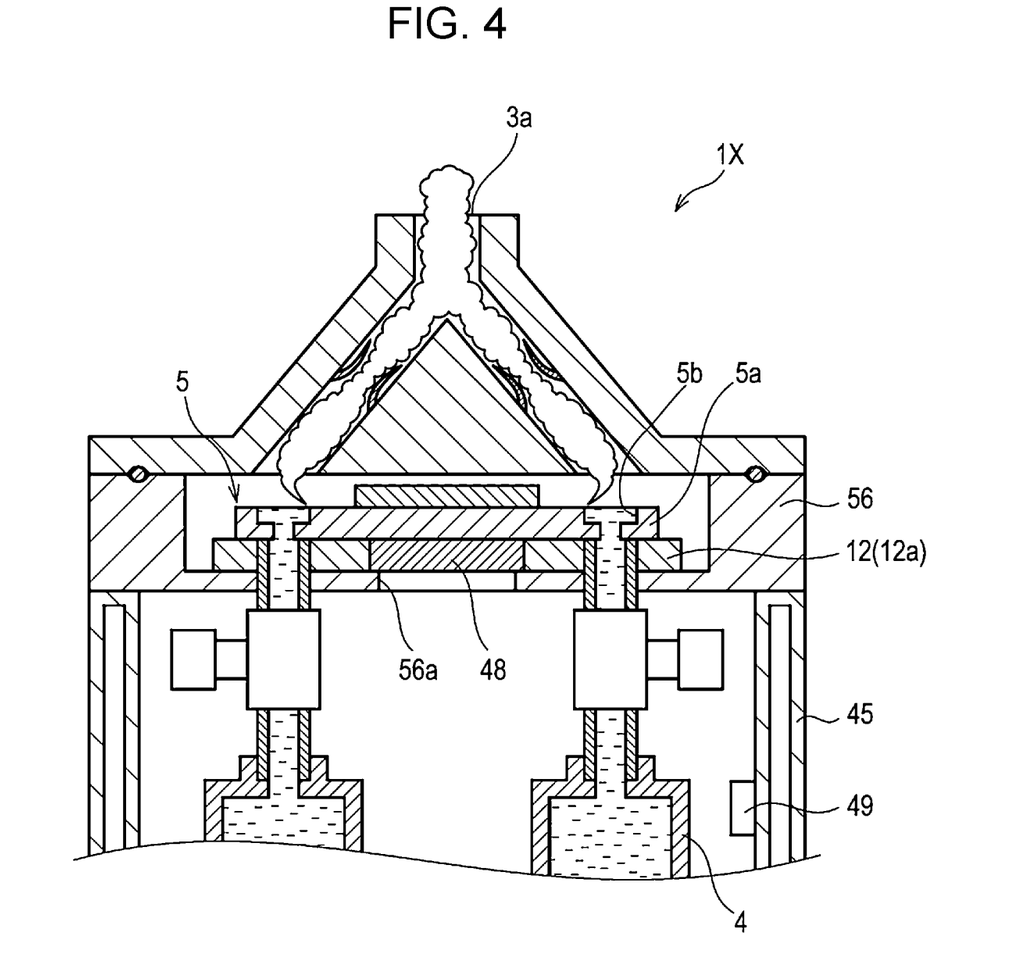
Figure 5:
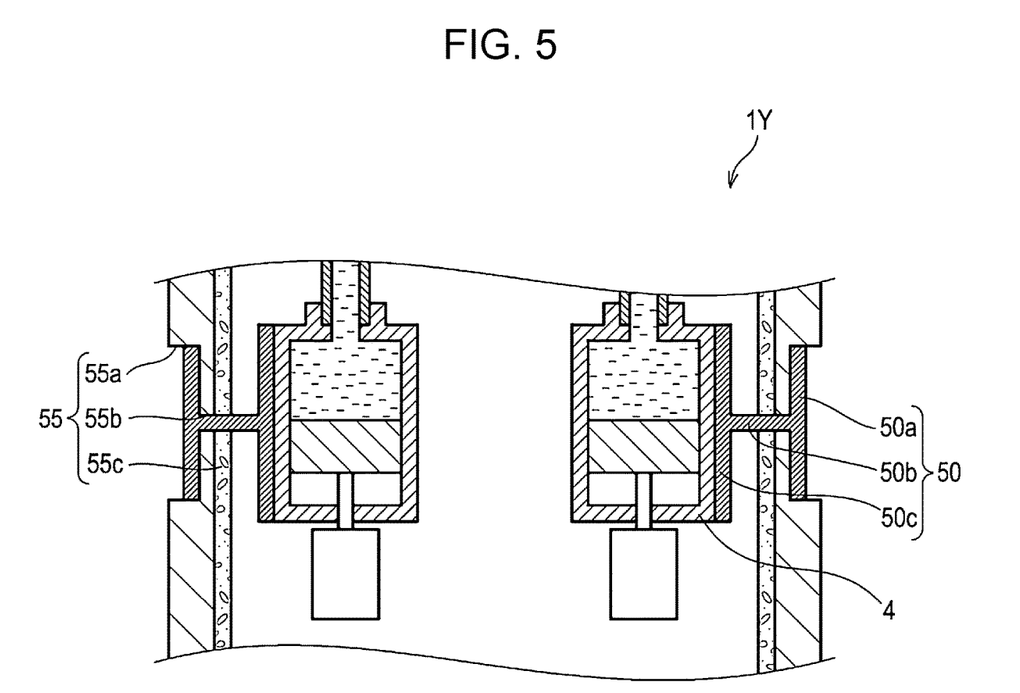

A temperature control part (Peltier element 48) according to a first modification is now described below with reference to mainly FIG. 4. FIG. 4 schematically illustrates an aerosol supply device 1X including the Peltier element 48 and the temperature sensor 49, in accordance with a first modification.

The temperature control part according to the first modification includes a cooling part (Peltier element 48) configured to absorb heat at a given location between the accommodating part (cartridge 4) and the storing part 5b.

In another example, the temperature control part may include a heating part (Peltier element 48) configured to release heat at a given location between the accommodating part (cartridge 4) and the storing part 5b.

According to the above-mentioned configuration, the temperature control part includes a cooling part (Peltier element 48) or a heating part (Peltier element 48) configured to cool or heat a given location between the accommodating part (cartridge 4) and the storing part 5b to control the temperature of the liquid 10 passing through the location to thereby stabilize the rate of atomization. In other words, the above-mentioned configuration helps to reduce the influence of outside air temperature.

In particular, using the Peltier element 48 as the cooling part is preferred in comparison to using an air-cooling device because at least a portion of the interior of the aerosol supply device 1X can be suitably cooled to a temperature less than or equal to the outside air temperature.

For example, the Peltier element 48 does not use a refrigerant such as chlorofluorocarbon and thus has very little impact on the environment. Further, the Peltier element 48 allows for compact/lightweight construction and flexible shape design, and makes it easily possible to avoid interference with other components within the device.

Further, the Peltier element 48 has superior temperature response, and is capable of both cooling and heating. Accordingly, the Peltier element 48 enables temperature control near room temperature, and the absence of any movable part eliminates any potential vibration/noise. Due to the absence of any mechanical component that is subject to fatigue/breakage, the Peltier element 48 allows for maximum lifetime and reliability as cooling means.

Further, the Peltier element 48 is operable only by electric wiring. The Peltier element 48 is thus easy to handle, is free from risks such as refrigerant gas leaks or corrosive liquid leaks, and allows for easy maintenance.

However, the cooling part according to the present invention may not necessarily be configured as described above. Alternatively, the cooling part may be formed by an air-cooling device such as a fan, a water-cooling device, or other devices (not illustrated).

In one example, the cooling part may include a passage through which water can be supplied from the outside to a target part to be cooled (e.g., the piezoelectric substrate 5a). In this case, air may be blown against the target part by a fan (not illustrated) to promote evaporation of water, and the resulting heat of vaporization may be used to cool the target part. In another example, a refrigerant such as chlorofluorocarbon or hydrofluorocarbon may be fed into the device, and the refrigerant may be rapidly expanded by an expansion valve (not illustrated) disposed within the device to thereby cool air that contacts the target part. The refrigerant may be made to circulate inside and outside the device as in the case of a heat pump.

In particular, the cooling part (Peltier element 48) or heating part (Peltier element 48) according to the first modification is positioned to provide cooling or heating to the piezoelectric substrate 5a.

The expression "positioned to provide cooling or heating" specifically means that the cooling part (Peltier element 48) or the heating part (Peltier element 48) is positioned to face the piezoelectric substrate 5a while being spaced from or in contact with the piezoelectric substrate 5a. The expression "positioned to provide cooling or heating" according to the embodiment means that the Peltier element 48 is positioned such that its upper surface is in contact with the lower surface of the piezoelectric substrate 5a.

The above-mentioned configuration makes it possible to control the temperature of the piezoelectric substrate 5a with which the liquid 10 comes into contact during atomization of the liquid 10. This allows the rate of atomization to be suitably controlled in comparison to a case where the temperature of a part remote from where atomization takes place is controlled.

In particular, disposing the cooling part (Peltier element 48) at the above-mentioned location allows the cooling part to suitably cool the piezoelectric substrate 5a, which tends to easily rise in temperature due to a surface acoustic wave generated thereon. This leads to extended lifetime of the piezoelectric substrate 5a.

More specifically, a lid 56 has a through-hole 56a provided in a part of the lid 56 facing the central portion of the lower surface of the Peltier element 48. Due to the presence of the through-hole 56a, the lower surface of the Peltier element 48 faces the internal space of the housing 45.

The above-mentioned configuration allows the Peltier element 48 to, under control by the controller 12a, release heat generated from the piezoelectric substrate 5a to the internal space of the housing 45.

The present invention is not limited to the configuration in which the Peltier element 48 according to the first modification is disposed directly under the piezoelectric substrate 5a. In other words, the Peltier element 48 may not necessarily be configured to release heat generated from the piezoelectric substrate 5a to the internal space of the housing 45.

For example, the Peltier element 48 may be configured to release heat generated from the piezoelectric substrate 5a to the outside of the aerosol supply device 1X. In other words, the Peltier element 48 may be configured to allow heat exchange in a desired direction between the inside of the housing 45 and the outside of the aerosol supply device 1X.

More specifically, the Peltier element 48 may be disposed in the housing 45 such that one side of the Peltier element 48 is exposed to the outside of the aerosol supply device 1X, and a side opposite to the one side of the Peltier element 48 is exposed to the internal space of the housing 45. According to the above-mentioned configuration, whether to provide cooling or heating to the internal space of the housing 45 can be switched simply by changing the direction of current to be passed through the Peltier element 48.

The temperature control part (heating part) is used to heat the cartridge 4 to prevent the liquid 10 from freezing within the cartridge 4 under low outside air temperature conditions or to melt the frozen liquid 10 into liquid form again. The temperature control unit used at this time is not limited to the Peltier element 48. Alternatively, for example, a heater (not illustrated) may not be used.

As described above with reference to FIG. 2, the aerosol supply device 1 according to the embodiment mentioned above includes the pump 9 capable of supplying the liquid 10 to the atomization unit 5, and the controller 12a configured to control the electric power to be supplied to the pump 9. In addition to these components, the aerosol supply device 1X according to the first modification further includes the temperature sensor 49 illustrated in FIG. 4. The temperature sensor 49 detects the temperature around the accommodating part (cartridge 4). The temperature sensor 49 includes, for example, a thermocouple or resistance temperature detector.

As with the pump 9 according to the first embodiment, the pump 9 is a syringe pump capable of pulling the liquid 10 back toward the accommodating part (cartridge 4) from the atomization unit 5.

The controller 12a is configured to receive a signal detected from the temperature sensor 49, and control the pump 9 such that when a temperature of the liquid 10 detected by the temperature sensor 49 is greater than or equal to a predetermined temperature or less than or equal to a predetermined temperature, the liquid 10 is pulled back toward the accommodating part from the liquid 10, or the liquid 10 is pushed out toward the atomization unit 5 from the accommodating part.

In one example, the "predetermined temperature" is a temperature represented by temperature information set in advance prior to product shipment and stored in the control board 12. In a further preferred example, the predetermined temperature is a variable temperature that can be set after product shipment, as this allows the temperature to be changed in accordance with the external environment, product condition, or other circumstances.

For instance, in summer when the outside air temperature is high, the liquid 10 expands, which may in some cases cause the liquid 10 to spill over from a predetermined area (e.g., the storing part 5b). Such a situation, that is, a situation where due to the influence of outside air temperature, the liquid 10 spills out from a predetermined area and is no longer atomized, can be prevented or reduced by pulling back the liquid 10 toward the accommodating part by means of the pump 9.

In winter when the outside air temperature is low, the liquid 10 contracts, and thus may not reach the atomization unit 5 in some cases. Such a situation, that is, a situation where due to the influence of outside air temperature, the liquid 10 does not reach the atomization unit 5 and is longer atomized, can be prevented or reduced by pushing out the liquid 10 toward the atomization unit 5 by means of the pump 9.

In other words, according to the above-mentioned configuration, the controller 12a controls the pump 9 to allow the liquid 10 to be kept at an appropriate position for atomization.

In another preferred example, the controller 12a is configured to, upon receiving a signal indicative of the power switch 15 being turned off, control the pump 9 such that the liquid 10 is pulled back into the cartridge 4 from the atomization unit 5. This helps to prevent leakage of the liquid from the storing part 5*b*.

In another preferred example, the controller 12*a* is configured to, upon receiving a signal indicative of the power switch 15 being turned on, control the pump 9 to feed the liquid 10 to an appropriate liquid position (e.g., the storing part 5*b*) and keep the liquid 10 on standby so that the liquid 10 is ready to be atomized whenever needed.

The controller 12*a* is configured to control the electric power to be supplied to a vibration source (such as the electrode 5*c* or a vibrating motor) such that: when the liquid 10 is at a first temperature, a first electric power is supplied to the vibration source; when the liquid 10 is at a second temperature lower than the first temperature, a second electric power greater than the first electric power is supplied to the vibration source; and when the liquid 10 is at a third temperature higher than the first temperature, a third electric power less than the first electric power is supplied to the vibration source.

In this regard, if the liquid 10 is at a high temperature, supplying to the electrode 5*c* the same electric power as that when the liquid 10 is at a low temperature results in increased rate of atomization due to low viscosity of the liquid 10 in comparison to when the liquid 10 is at a low temperature. Accordingly, the electric power to be supplied to the electrode 5*c* is decreased to thereby reduce variations in the rate of atomization.

Conversely, if the liquid 10 is at a low high temperature, supplying to the electrode 5*c* the same electric power as that when the liquid 10 is at a high temperature results in decreased rate of atomization due to high viscosity of the liquid 10 in comparison to when the liquid 10 is at a high temperature. Accordingly, the electric power to be supplied to the electrode 5*c* is increased to thereby reduce variations in the rate of atomization.

According to the above-mentioned configuration, by controlling the electric power to be supplied to the vibration source (such as the electrode 5*c* or a vibrating motor), the amount of aerosol 11 generated by atomization can be finely controlled. This helps to stabilize the rate of atomization.

In a particularly preferred example, the temperature of the liquid under a low temperature condition (e.g., the second temperature mentioned above) when the rate of atomization is low is used as a reference temperature, and based on the reference temperature, the amount of electric power to be supplied to the electrode 5*c* is set so as to provide a sufficient rate of atomization of the liquid 10 in a stable manner.

The term "temperature of the liquid 10" as used herein refers to a temperature calculated based on a temperature detected by the temperature sensor 49 disposed near the cartridge 4 (within the space around the cartridge 4). However, this is not meant to be limiting. Alternatively, the above-mentioned temperature may be a temperature directly detected by a temperature sensor (not illustrated) disposed in direct contact with the liquid 10.

[Second Modification]

Lastly, a temperature control part (external-heat conduction part 50) and a heat insulation structure (urethane foam 55*c*) according to a second modification are described below with reference to mainly FIG. 5. FIG. 5 schematically illustrates a housing 55 with the urethane foam 55*c* attached thereto, and the external-heat conduction part 50, in accordance with the second modification.

An aerosol supply device 1Y according to the second modification includes the housing 55 facing the outside of the aerosol supply device 1Y and covering at least the accommodating part (cartridge 4). The temperature control part includes the external-heat conduction part 50. The external-heat conduction part 50 has thermal conductivity, and is connected to the accommodating part (cartridge 4) and to the outer surface of the housing 55. As used herein, the expression "having thermal conductivity" means being highly thermally conductive. Accordingly, the external-heat conduction part 50 includes a material such as copper, aluminum, or carbon. More specifically, the external-heat conduction part 50 has a higher thermal conductivity than another component (which is, for example, the housing 55 in accordance with the embodiment) disposed at a location between the outside and the cartridge 4.

The external-heat conduction part 50 includes an exposed part 50*a*, an introduction part 50*b*, and a contact part 50*c*. The exposed part 50*a* is an externally exposed part. The introduction part 50*b* is connected to the exposed part 50*a* via a through-hole 55*b*, which is provided in the housing 55, to introduce heat inward. The contact part 50*c* is connected to the introduction part 50*b*, and contacts the cartridge 4.

The exposed part 50*a* is disposed in a depression 55*a* provided in the outer surface of the housing 55. The depression 55*a* is provided in at least a portion of the outer surface of the housing 55 (at the same position as the cartridge 4 in the axial direction in accordance with the embodiment).

The exposed part 50*a* is disposed closer to the bottom of the depression 55*a* than to the outer edge of the depression 55*a*. This configuration helps to ensure that another object does not come into contact with the exposed part 50*a* unless intended otherwise. This makes it possible to reduce unexpected propagation of heat to the exposed part 50*a* from the other object.

According to the above-mentioned configuration, heat is supplied from the outside to the accommodating part (cartridge 4) or dissipated from the accommodating part (cartridge 4) to the outside through the outer surface of the housing 55. This makes it possible to control the temperature of the liquid 10 within the accommodating part (cartridge 4).

Examples of means for supplying external heat include one utilizing body temperature (human hand) and one utilizing chemical heat generation (portable heat pack).

The heat conduction part (element-heat conduction part 40 or external-heat conduction part 50) may be formed with a cylindrical or box-shaped part so as to surround the cartridge 4.

Although the heat insulation structure of the aerosol supply device 1 according to the first embodiment illustrated in FIG. 2 is described above as being formed by the vacuum area 45*a*, this is not meant to be limiting. For example, the aerosol supply device 1Y according to the second modification includes a heat insulation structure formed by the urethane foam 55*c* bonded by using an adhesive so as to cover the inner surface of the housing 55. Using the urethane foam 55*c* allows a heat insulation structure to be formed easily. The urethane foam 55*c* has a through-hole provided in a portion of the urethane foam 55*c*. The introduction part 50*b* of the external-heat conduction part 50 can be inserted through the through-hole.

Each of the aerosol supply devices 1, 1X, and 1Y according to the embodiment and their modifications mentioned above is described above as being configured to atomize a liquid by using a SAW. However, the aerosol supply device according to the present invention may not necessarily be an aerosol supply device that atomizes a liquid by using a SAW, but may be an aerosol supply device that atomizes a liquid by using, for example, a heating device such as a heater, or an ultrasonic wave oscillator.

Examples of aerosol supply devices other than electronic cigarettes may include inhalers for ejecting a liquid, and diffusers for diffusing fragrance.

Although the foregoing description of the embodiment is directed to an exemplary configuration in which the liquid 10 is supplied toward the piezoelectric substrate 5a from below, this is not meant to be limiting. Alternatively, the liquid 10 may be configured to drip onto the piezoelectric substrate 5a from above.

Although the foregoing description of the embodiment and their modifications mentioned above is directed to a case where the housing 45 and the lid 56 are separate components constituting the device body 2, this is not meant to be limiting of the present invention. Alternatively, the housing 45 and the lid 56 may be formed integrally.

In another example, individual components of the aerosol supply device according to the present invention may not necessarily exist as independent components. For instance, the following cases may be permitted: plural components are formed as a single part; a single component is formed by plural components; a component constitutes a portion of another component; and a component and another component partially overlap.

It is to be readily appreciated that the features described above with reference to the embodiment and their modifications mentioned above can be used in combination. For example, the aerosol supply device may include, as a temperature control part, all of the following components: the element-heat conduction part 40, the Peltier element 48, and the external-heat conduction part 50.

The present application claims priority from Japanese Patent Application No. 2019-074361 filed on Apr. 9, 2019, the entire contents of which are hereby incorporated by reference.

The embodiment described in the foregoing encompass technical ideas described below.

(1) An aerosol supply device including:
an accommodating part configured to accommodate a liquid;
an atomization unit having a storing part to store the liquid supplied from the accommodating part, the atomization unit being configured to generate an aerosol by atomizing the liquid stored in the storing part; and
a temperature control part configured to control a temperature of the liquid at a given location between the accommodating part and the storing part.

(2) The aerosol supply device according to (1),
wherein the aerosol supply device is configured to supply the aerosol by atomizing the liquid by vibration,
wherein the atomization unit includes
a vibrating element configured to vibrate the liquid to form the aerosol, and
a vibration source configured to, in response to receiving supply of electric power, vibrate the vibrating element,
wherein the aerosol supply device further includes an element-heat conduction part having thermal conductivity, the element-heat conduction unit being connected to the vibrating element and to the accommodating part, and
wherein the temperature control part includes the vibrating element, the vibration source, and the element-heat conduction part.

(3) The aerosol supply device according to (1) or (2),
wherein the aerosol supply device is configured to supply the aerosol by atomizing the liquid by vibration,
wherein the atomization unit includes
a vibrating element configured to vibrate the liquid to form the aerosol, and
a vibration source configured to, in response to receiving supply of electric power, vibrate the vibrating element,
wherein the aerosol supply device further includes a controller configured to control the electric power to be supplied to the vibration source, and
wherein the controller is configured to,
when the liquid is at a first temperature, supply a first electric power as the electric power,
when the liquid is at a second temperature lower than the first temperature, supply a second electric power greater than the first electric power as the electric power, and
when the liquid is at a third temperature higher than the first temperature, supply a third electric power less than the first electric power as the electric power.

(4) The aerosol supply device according to (2) or (3),
wherein the aerosol supply device is configured to supply the aerosol by atomizing the liquid by a surface acoustic wave,
wherein the vibrating element is a piezoelectric substrate having a piezoelectric element, and
wherein the vibration source is a comb-shaped electrode configured to generate a surface acoustic wave on the piezoelectric substrate.

(5) The aerosol supply device according to any one of (1) to (4), wherein a heat insulation structure is disposed between the accommodating part and an outside of the aerosol supply device, the heat insulation structure having a lower thermal conductivity than the accommodating part.

(6) The aerosol supply device according to any one of (1) to (5), further including
a housing facing an outside of the aerosol supply device and covering at least the accommodating part, and
wherein the temperature control part includes an external-heat conduction part having thermal conductivity, the external-heat conduction part being connected to the accommodating part and to an outer surface of the housing.

(7) The aerosol supply device according to any one of (1) to (6), wherein the temperature control part includes a cooling part configured to absorb heat, or a heating part configured to release heat, at a given location between the accommodating part and the storing part.

(8) The aerosol supply device according to any one of (1) to (7), wherein the temperature control part includes a heating part configured to release heat at a given location between the accommodating part and the storing part.

(9) The aerosol supply device according to (8) as dependent on (7),
wherein the aerosol supply device is configured to supply the aerosol by atomizing the liquid by a surface acoustic wave,
wherein the atomization unit includes
a piezoelectric substrate having a piezoelectric element, the piezoelectric substrate being configured to vibrate the liquid to form the aerosol, and
a comb-shaped electrode configured to, in response to receiving supply of electric power, generate a surface acoustic wave on the piezoelectric substrate, and
wherein the cooling part or the heating part is positioned to provide cooling or heating to the piezoelectric substrate.

(10) The aerosol supply device according to any one of (1) to (9), wherein the temperature control part includes a Peltier element.

(11) The aerosol supply device according to any one of (1) to (10), further including:
a pump capable of supplying the liquid to the atomization unit;

a controller configured to control electric power to be supplied to the pump; and a temperature sensor configured to detect a temperature around the accommodating part, wherein the pump is a syringe pump capable of pulling back the liquid toward the accommodating part from the atomization unit, and wherein the controller is configured to, when a temperature of the liquid detected by the temperature sensor is greater than or equal to a predetermined temperature or less than or equal to a predetermined temperature, control the pump to pull back the liquid toward the accommodating part from the atomization unit or to push out the liquid toward the atomization unit from the accommodating part.

REFERENCE SIGNS LIST 1, 1X, 1Y aerosol supply device
2 device body
3 mouthpiece
   3a discharge port
4 cartridge (accommodating part)
   4a body part
   4b base plate
   4c through-hole
   4d sliding block
5 atomization unit
   5a piezoelectric substrate (substrate, vibrating element, temperature control part)
   5b storing part
   5c electrode (vibration source, temperature control part)
   5d through-hole
6 first passage
   6a tube
7 second passage
8 volatilization preventing part
   8a solenoid valve
   8b duckbill valve
9 pump
   9a motor
   9b push rod
10 liquid
11 aerosol
12 control board
   12a controller
13 power board
14 battery
15 power switch
40 element-heat conduction part (temperature control part)
41 thermostat (temperature control part)
45 housing
   45a vacuum area (heat insulation structure)
46 lid
48 Peltier element (cooling part, heating part, temperature control part)
49 temperature sensor
50 external-heat conduction part (temperature control part)
   50a exposed part
   50b introduction part
   50c contact part
55 housing
   55a depression
   55b through-hole
   55c urethane foam (heat insulation structure)
56 lid
   56a through-hole

The invention claimed is:

1. An aerosol supply device comprising:
an accommodating part configured to accommodate a liquid;
an atomization unit having a storing part to store the liquid supplied from the accommodating part, the atomization unit being configured to generate an aerosol by atomizing the liquid stored in the storing part;
a temperature control part configured to control a temperature of the liquid at a given location between the accommodating part and the storing part; and
a housing provided on an outside of the aerosol supply device to surround at least the accommodating part,
wherein the temperature control part includes an external-heat conduction part having thermal conductivity, the external-heat conduction part being connected to the accommodating part and to an outer surface of the housing.

2. The aerosol supply device according to claim 1, wherein the temperature control part includes a cooling part configured to absorb heat at a given location between the accommodating part and the storing part.

3. The aerosol supply device according to claim 2, wherein the temperature control part includes a heating part configured to release heat at a given location between the accommodating part and the storing part.

4. The aerosol supply device according to claim 3, wherein the aerosol supply device is configured to supply the aerosol by atomizing the liquid by a surface acoustic wave,
wherein the atomization unit includes
a piezoelectric substrate having a piezoelectric element, the piezoelectric substrate being configured to vibrate the liquid to form the aerosol, and
a comb-shaped electrode configured to, in response to receiving supply of electric power, generate a surface acoustic wave on the piezoelectric substrate, and
wherein the cooling part or the heating part is positioned to provide cooling or heating to the piezoelectric substrate.

5. The aerosol supply device according to claim 1, wherein the aerosol supply device is configured to supply the aerosol by atomizing the liquid by vibration,
wherein the atomization unit includes
a vibrating element configured to vibrate the liquid to form the aerosol, and
a vibration source configured to, in response to receiving supply of electric power, vibrate the vibrating element,
wherein the aerosol supply device further includes an element-heat conduction part having thermal conductivity, the element-heat conduction part being connected to the vibrating element and to the accommodating part, and
wherein the temperature control part includes the vibrating element, the vibration source, and the element-heat conduction part.

6. The aerosol supply device according to claim 5, wherein the aerosol supply device is configured to supply the aerosol by atomizing the liquid by a surface acoustic wave,
wherein the vibrating element is a piezoelectric substrate having a piezoelectric element, and wherein the vibration source is a comb-shaped electrode configured to generate a surface acoustic wave on the piezoelectric substrate.

7. The aerosol supply device according to claim 1, wherein the aerosol supply device is configured to supply the aerosol by atomizing the liquid by vibration,
wherein the atomization unit includes
a vibrating element configured to vibrate the liquid to form the aerosol, and
a vibration source configured to, in response to receiving supply of electric power, vibrate the vibrating element,
wherein the aerosol supply device further includes a controller configured to control the electric power to be supplied to the vibration source, and
wherein the controller is configured to,
when the liquid is at a first temperature, supply a first electric power as the electric power,
when the liquid is at a second temperature lower than the first temperature, supply a second electric power greater than the first electric power as the electric power, and
when the liquid is at a third temperature higher than the first temperature, supply a third electric power less than the first electric power as the electric power.

8. The aerosol supply device according to claim 1, wherein the temperature control part includes a heating part configured to release heat at a given location between the accommodating part and the storing part.

9. The aerosol supply device according to claim 1, wherein the temperature control part includes a Peltier element.

10. The aerosol supply device according to claim 1, wherein a heat insulation structure having a lower thermal conductivity than the accommodating part is formed by a vacuum area between an inner layer and an outer layer of the housing.

11. The aerosol supply device according to claim 1, wherein the external-heat conduction part has a first section connected to the accommodating part, a second section contacting an outer surface of the housing and a third section extending through the housing and connected to the first section and the second section.

12. The aerosol supply device according to claim 1, further comprising:
a pump capable of supplying the liquid to the atomization unit;
a controller configured to control electric power to be supplied to the pump; and
a temperature sensor configured to detect a temperature around the accommodating part,
wherein the pump is a syringe pump capable of pulling back the liquid toward the accommodating part from the atomization unit, and
wherein the controller is configured to, when a temperature of the liquid detected by the temperature sensor is greater than or equal to a predetermined temperature or less than or equal to a predetermined temperature, control the pump to pull back the liquid toward the accommodating part from the atomization unit or to push out the liquid toward the atomization unit from the accommodating part.

* * * * *